United States Patent
Jorgensen et al.

(10) Patent No.: US 11,819,390 B2
(45) Date of Patent: *Nov. 21, 2023

(54) TAMPON PLEDGET FOR INCREASED BYPASS LEAKAGE PROTECTION

(71) Applicant: Edgewell Personal Care Brands, LLC, Chesterfield, MO (US)

(72) Inventors: Robert Jorgensen, Middletown, DE (US); Keith Edgett, Middletown, DE (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 966 days.

This patent is subject to a terminal disclaimer.

(21) Appl. No.: 16/777,957

(22) Filed: Jan. 31, 2020

(65) Prior Publication Data

US 2020/0163806 A1   May 28, 2020

Related U.S. Application Data

(63) Continuation of application No. 15/486,470, filed on Apr. 13, 2017, now Pat. No. 10,596,046, which is a
(Continued)

(51) Int. Cl.
*A61F 13/20* (2006.01)
*A61F 13/15* (2006.01)
(Continued)

(52) U.S. Cl.
CPC ...... *A61F 13/208* (2013.01); *A61F 13/15203* (2013.01); *A61F 13/2025* (2013.01);
(Continued)

(58) Field of Classification Search
CPC ............. A61F 13/208; A61F 13/15203; A61F 13/2028; A61F 13/2065; A61F 13/2068;
(Continued)

(56) References Cited

U.S. PATENT DOCUMENTS 1,401,358 A   12/1921   Peterkin
2,330,257 A    9/1943   Bailey
(Continued)

FOREIGN PATENT DOCUMENTS

BE   768046 A    11/1971
CA   2127144 A   10/1995
(Continued)

OTHER PUBLICATIONS

Examination Report for corresponding GB Application No. GB1117582.5, dated Mar. 27, 2013, pp. 1-2.
(Continued)

*Primary Examiner* — Susan S Su

(57) ABSTRACT

There is provided a tampon pledget that includes one or more enhanced features that result in the pledget exhibiting increased bypass leakage prevention. These enhanced features may include, but are not limited to, geometry, absorption, and any combinations thereof. There is also provided one or more methods for constructing a tampon pledget having increased bypass leakage protection.

20 Claims, 2 Drawing Sheets

Related U.S. Application Data continuation of application No. 15/157,792, filed on May 18, 2016, now Pat. No. 9,687,389, which is a continuation of application No. 14/972,442, filed on Dec. 17, 2015, now Pat. No. 10,076,452, which is a continuation of application No. 12/958,897, filed on Dec. 2, 2010, now Pat. No. 9,259,360, which is a continuation of application No. 11/983,264, filed on Nov. 8, 2007, now Pat. No. 7,867,209.

(60) Provisional application No. 60/857,694, filed on Nov. 8, 2006.

(51) Int. Cl.
  *A61L 15/28* (2006.01)
  *A61L 15/42* (2006.01)
  *A61L 15/60* (2006.01)

(52) U.S. Cl.
  CPC ...... *A61F 13/2028* (2013.01); *A61F 13/2057* (2013.01); *A61F 13/2065* (2013.01); *A61F 13/2068* (2013.01); *A61F 13/2088* (2013.01); *A61L 15/28* (2013.01); *A61L 15/425* (2013.01); *A61L 15/60* (2013.01); *A61F 2013/15447* (2013.01)

(58) Field of Classification Search
  CPC ........ A61F 2013/15447; A61F 13/2022; A61F 13/2025
  See application file for complete search history.

(56) References Cited

U.S. PATENT DOCUMENTS

| | | |
|---|---|---|
| 2,391,343 A | 12/1945 | Popper |
| 2,412,861 A | 12/1946 | Beadle et al. |
| 2,499,414 A | 3/1950 | Rabell |
| 2,761,449 A | 9/1956 | Bletzinger |
| 3,051,177 A | 8/1962 | Wilson |
| 3,079,921 A | 3/1963 | Brecht et al. |
| 3,340,874 A | 9/1967 | Burgeni |
| 3,371,666 A | 3/1968 | Lewing |
| 3,397,695 A | 8/1968 | Voss |
| 3,465,390 A | 9/1969 | Mooney |
| 3,572,341 A | 3/1971 | Glassman |
| 3,606,643 A | 9/1971 | Mooney |
| 3,610,243 A | 10/1971 | Jones, Sr. |
| 3,618,605 A | 11/1971 | Glassman |
| 3,628,534 A | 12/1971 | Donohue |
| 3,643,661 A | 2/1972 | Crockford |
| 3,683,912 A | 8/1972 | Olson et al. |
| 3,695,270 A | 10/1972 | Dostal |
| 3,699,965 A | 10/1972 | Dostal |
| 3,712,305 A | 1/1973 | Wennerblom et al. |
| 3,731,687 A | 5/1973 | Glassman |
| RE27,677 E | 6/1973 | Glassman |
| 3,738,364 A | 6/1973 | Brien et al. |
| 3,749,094 A | 7/1973 | Duncan |
| 3,811,445 A | 5/1974 | Dostal |
| 3,834,389 A | 9/1974 | Dulle |
| 3,981,305 A | 9/1976 | Ring |
| 4,200,101 A | 4/1980 | Glassman |
| 4,212,301 A | 7/1980 | Johnson |
| 4,274,412 A | 6/1981 | Austin |
| 4,318,407 A | 3/1982 | Woon |
| 4,335,720 A | 6/1982 | Glassman |
| 4,335,721 A | 6/1982 | Matthews |
| 4,373,529 A | 2/1983 | Lilaonitkul et al. |
| 4,374,522 A | 2/1983 | Olevsky |
| 4,627,849 A | 12/1986 | Walton et al. |
| 4,787,895 A | 11/1988 | Stokes et al. |
| 4,836,587 A | 6/1989 | Hinzmann |
| 4,973,302 A | 11/1990 | Armour et al. |
| 5,004,467 A | 4/1991 | Hinzmann et al. |
| 5,006,116 A | 4/1991 | Alikhan et al. |
| 5,047,024 A | 9/1991 | Glassman |
| 5,112,348 A | 5/1992 | Glassman |
| 5,149,332 A | 9/1992 | Walton et al. |
| 5,153,971 A | 10/1992 | Van Iten |
| 5,314,743 A | 5/1994 | Meirowitz et al. |
| 5,364,383 A | 11/1994 | Hayes et al. |
| 5,389,067 A | 2/1995 | Rejai |
| 5,443,776 A | 8/1995 | Bartholomew et al. |
| 5,471,820 A | 12/1995 | Oppe et al. |
| 5,634,248 A | 6/1997 | McNelis et al. |
| 5,659,934 A | 8/1997 | Jessup et al. |
| 5,681,894 A | 10/1997 | Williams et al. |
| 5,755,906 A | 5/1998 | Achter et al. |
| 5,788,910 A | 8/1998 | McNelis et al. |
| 5,795,346 A | 8/1998 | Achter et al. |
| 5,804,653 A | 9/1998 | Weng |
| 5,807,372 A | 9/1998 | Balzar |
| 5,827,256 A | 10/1998 | Balzar |
| 5,873,971 A | 2/1999 | Balzar |
| 5,891,081 A | 4/1999 | McNelis et al. |
| 5,891,123 A | 4/1999 | Balzar |
| 5,931,803 A | 8/1999 | Jackson |
| 5,986,000 A | 11/1999 | Williams et al. |
| 6,039,716 A | 3/2000 | Jessup et al. |
| 6,039,828 A | 3/2000 | Achter et al. |
| 6,045,526 A | 4/2000 | Jackson |
| 6,142,984 A | 11/2000 | Brown et al. |
| 6,177,608 B1 | 1/2001 | Weinstrauch |
| 6,179,802 B1 | 1/2001 | Jackson |
| 6,183,436 B1 | 2/2001 | Korteweg et al. |
| 6,186,994 B1 | 2/2001 | Bowles et al. |
| 6,186,995 B1 | 2/2001 | Tharpe, Jr. |
| 6,248,274 B1 | 6/2001 | Williams |
| 6,333,108 B1 | 12/2001 | Wilkes et al. |
| 6,353,146 B1 | 3/2002 | Williams |
| 6,419,777 B1 | 7/2002 | Achter et al. |
| 6,478,726 B1 | 11/2002 | Zunker |
| 6,506,958 B2 | 1/2003 | Williams |
| 6,511,452 B1 | 1/2003 | Rejai et al. |
| 6,558,370 B2 | 5/2003 | Moser |
| 6,585,300 B1 | 7/2003 | Rajala et al. |
| 6,595,974 B1 | 7/2003 | Pauley et al. |
| 6,596,919 B2 | 7/2003 | Williams |
| 6,603,054 B2 | 8/2003 | Chen et al. |
| 6,635,205 B2 | 10/2003 | Williams et al. |
| 6,635,800 B2 | 10/2003 | Jackson et al. |
| 6,682,513 B2 | 1/2004 | Agyapong et al. |
| 6,702,797 B2 | 3/2004 | Williams |
| 6,719,743 B1 | 4/2004 | Wada |
| 6,740,070 B2 | 5/2004 | Agyapong et al. |
| D492,033 S | 6/2004 | Jarmon et al. |
| 6,746,418 B1 | 6/2004 | Pauley et al. |
| 6,814,722 B2 | 11/2004 | Brown et al. |
| 6,830,554 B2 | 12/2004 | Jackson et al. |
| 6,886,443 B2 | 5/2005 | Rejai |
| 6,887,226 B2 | 5/2005 | Cassoni et al. |
| 6,890,324 B1 | 5/2005 | Jackson et al. |
| 6,923,789 B2 | 8/2005 | Lemay et al. |
| 6,932,805 B2 | 8/2005 | Kollwitz et al. |
| 6,953,456 B2 | 10/2005 | Fuchs et al. |
| 7,044,928 B2 | 5/2006 | Lemay et al. |
| 7,160,279 B2 | 1/2007 | Pauley et al. |
| 7,226,436 B2 | 6/2007 | Gorham et al. |
| 7,250,129 B2 | 7/2007 | Williams et al. |
| 7,335,194 B2 | 2/2008 | Wada |
| 7,387,622 B1 | 6/2008 | Pauley et al. |
| D572,362 S | 7/2008 | Edgett et al. |
| D579,113 S | 10/2008 | Edgett et al. |
| 7,563,401 B2 | 7/2009 | Pham et al. |
| D612,940 S | 3/2010 | Edgett et al. |
| 7,678,095 B2 | 3/2010 | Jackson et al. |
| 7,704,242 B2 | 4/2010 | Lemay et al. |
| 7,727,208 B2 | 6/2010 | Lemay et al. |
| 7,727,210 B2 | 6/2010 | Lemay et al. |
| 7,745,686 B2 | 6/2010 | Mauro et al. |
| 7,780,892 B2 | 8/2010 | Miller et al. |
| 7,798,986 B2 | 9/2010 | Melvin et al. |
| 7,799,966 B2 | 9/2010 | Williams et al. |

(56) References Cited

U.S. PATENT DOCUMENTS

| | | | |
|---|---|---|---|
| 7,815,594 | B2 | 10/2010 | Dougherty, Jr. et al. |
| D626,650 | S | 11/2010 | Edgett et al. |
| 7,862,533 | B2 | 1/2011 | Lemay et al. |
| 7,867,209 | B2 | 1/2011 | Jorgensen et al. |
| 7,887,525 | B2 | 2/2011 | Gorham et al. |
| 8,070,710 | B2 | 12/2011 | Dougherty |
| 8,093,446 | B2 | 1/2012 | Knuth et al. |
| 8,166,834 | B2 | 5/2012 | Dougherty, Jr. et al. |
| 8,197,434 | B2 | 6/2012 | Lemay et al. |
| 8,198,504 | B2 | 6/2012 | Glaug et al. |
| 8,221,375 | B2 | 7/2012 | Lemay et al. |
| 8,323,256 | B2 | 12/2012 | Edgett et al. |
| 8,372,027 | B2 | 2/2013 | Lemay et al. |
| 8,444,590 | B2 | 5/2013 | Lemay et al. |
| 8,556,845 | B2 | 10/2013 | Lemay et al. |
| 8,571,883 | B2 | 10/2013 | Dougherty, Jr. et al. |
| 8,585,668 | B2 | 11/2013 | Pauley et al. |
| 8,696,957 | B2 | 4/2014 | Dougherty, Jr. et al. |
| 8,735,647 | B2 | 5/2014 | Schoelling |
| 8,827,974 | B2 | 9/2014 | Schmidt-Forst |
| 8,961,449 | B2 | 2/2015 | Jorgensen et al. |
| 9,107,775 | B2 | 8/2015 | Edgett et al. |
| 9,125,771 | B2 | 9/2015 | Schoelling |
| 9,173,778 | B2 | 11/2015 | Schoelling |
| 9,192,522 | B2 | 11/2015 | Edgett et al. |
| 2002/0120243 | A1 | 8/2002 | Kraemer et al. |
| 2002/0156442 | A1 | 10/2002 | Jackson et al. |
| 2003/0131456 | A1 | 7/2003 | Rajala et al. |
| 2003/0149416 | A1 | 8/2003 | Cole et al. |
| 2003/0158533 | A1 | 8/2003 | Agyapong et al. |
| 2003/0208180 | A1 | 11/2003 | Fuchs et al. |
| 2003/0225389 | A1 | 12/2003 | Cassoni et al. |
| 2004/0019317 | A1 | 1/2004 | Takagi et al. |
| 2004/0126555 | A1 | 7/2004 | Hartmann et al. |
| 2004/0193131 | A1 | 9/2004 | Wada |
| 2005/0059944 | A1 | 3/2005 | Jackson et al. |
| 2005/0096619 | A1 | 5/2005 | Costa |
| 2007/0016156 | A1* | 1/2007 | Burgdorf ............ A61F 13/2077 604/385.18 |
| 2007/0026228 | A1 | 2/2007 | Hartmann et al. |
| 2007/0260211 | A1 | 11/2007 | Schmidt-Forst |
| 2008/0065041 | A1 | 3/2008 | Stan et al. |
| 2008/0097366 | A1 | 4/2008 | Mathews |
| 2008/0110005 | A1 | 5/2008 | Gilbert et al. |
| 2008/0119811 | A1 | 5/2008 | Gilbert et al. |
| 2008/0221502 | A1 | 9/2008 | Binner et al. |
| 2008/0262464 | A1 | 10/2008 | Hasse et al. |
| 2008/0287902 | A1 | 11/2008 | Edgett et al. |
| 2009/0036859 | A1 | 2/2009 | Dougherty, Jr. et al. |
| 2009/0082712 | A1 | 3/2009 | Hasse et al. |
| 2009/0156979 | A1 | 6/2009 | Andersch |
| 2009/0227975 | A1 | 9/2009 | Dougherty, Jr. et al. |
| 2009/0234268 | A1 | 9/2009 | Jorgensen, Jr. et al. |
| 2009/0247981 | A1 | 10/2009 | Glaug et al. |
| 2009/0281474 | A1 | 11/2009 | Dougherty, Jr. et al. |
| 2009/0281514 | A1 | 11/2009 | Glaug et al. |
| 2010/0036309 | A1 | 2/2010 | Jorgensen, Jr. et al. |
| 2010/0056981 | A1 | 3/2010 | Karapasha et al. |
| 2010/0120707 | A1 | 5/2010 | Dougherty, Jr. et al. |
| 2010/0198133 | A1 | 8/2010 | Dougherty, Jr. et al. |
| 2011/0224637 | A1 | 9/2011 | Edgett et al. |
| 2012/0061867 | A1 | 3/2012 | Dougherty, Jr. et al. |
| 2013/0018347 | A1 | 1/2013 | Edgett et al. |
| 2014/0265026 | A1 | 9/2014 | Schoelling |
| 2014/0276523 | A1 | 9/2014 | Schoelling |
| 2015/0105711 | A1 | 4/2015 | Lemay et al. |
| 2015/0320608 | A1 | 11/2015 | Edgett et al. |

FOREIGN PATENT DOCUMENTS

| | | |
|---|---|---|
| CA | 2180789 A | 1/1997 |
| CA | 2312666 A1 | 1/2001 |
| CA | 108982 S | 8/2006 |
| CA | 115880 S | 8/2008 |
| CA | 2441647 A1 | 5/2009 |
| FR | 2207687 A1 | 6/1974 |
| FR | 2505176 A | 11/1982 |
| GB | 1108197 A | 4/1968 |
| GB | 2073592 | 10/1981 |
| GB | 2276395 A | 9/1994 |
| IE | 8904080 A | 6/1995 |
| IL | 109027 A | 2/1997 |
| JP | SHO44004240 | 2/1944 |
| JP | 62-8754 | 1/1987 |
| JP | 63-212358 A | 9/1988 |
| JP | H05-68695 | 3/1993 |
| JP | 2001-008964 | 1/2001 |
| JP | 2005-526584 | 9/2005 |
| JP | SHO62-027952 | 9/2005 |
| WO | 9933428 A1 | 7/1999 |
| WO | 0006071 A1 | 2/2000 |
| WO | 0124729 A1 | 4/2001 |
| WO | 0166055 A1 | 9/2001 |
| WO | 02058587 A1 | 8/2002 |
| WO | 2003101362 A2 | 12/2003 |
| WO | 2005041883 A1 | 5/2005 |
| WO | 2005112856 A1 | 12/2005 |
| WO | 2005112862 A1 | 12/2005 |
| WO | 2006016933 A1 | 2/2006 |
| WO | 2007078413 A1 | 7/2007 |
| WO | 2008009331 A1 | 1/2008 |
| WO | 2008056339 A1 | 5/2008 |
| WO | 2008144624 A1 | 11/2008 |
| ZA | 8803191 B | 11/1988 |
| ZA | 9706745 B | 2/1998 |

OTHER PUBLICATIONS

English Translation of Decision of Rejection against Japanese Patent Application No. 2012-506079; dated Jan. 7, 2013; pp. 1-4.
International Search Report for PCT/US2010/030351 dated Jun. 3, 2010.
PCT International Search Report, International Application No. PCT/US2008/064074, International Filing Date May 19, 2008, dated Jul. 21, 2008.
First Office Action Against JP Application No. 2010-508629, dated Dec. 20, 2011.
International Search Report dated Jun. 2, 2008, for International application No. PCT/*S07/13749.
Written Opinion dated Jun. 2, 2008, for International application No. PCT/US07/13749.
English Translation of Decision of Rejection against Japanese Patent Application No. 2010-508629; dated Dec. 27, 2012; pp. 1-3.
Unofficial English translation of First Office Action dated Feb. 13, 2012, from Japanese Application No. 2009-536296.
Supplemental European Search Report dated Aug. 5, 2011, from European Application No. 07839986.2.
Office Action dated Apr. 11, 2011 for corresponding Korean Patent Application No. 10-2009-7011433 with English summary of Office Action.
Examination Report for Canadian Patent Application No. 2669469 dated Dec. 1, 2010.
2005 Playtex Gentle Glide Plastic Tampons.
Office Action dated Jun. 3, 2019 for U.S. Appl. No. 15/486,470.

* cited by examiner

TAMPON PLEDGET FOR INCREASED BYPASS LEAKAGE PROTECTION

CROSS REFERENCE TO RELATED PATENT APPLICATIONS

This application is a continuation application of pending U.S. patent application Ser. No. 15/486,470, filed Apr. 13, 2017, which is a continuation of U.S. patent application Ser. No. 15/157,792, filed May 18, 2016, now U.S. Pat. No. 9,687,389, which is a continuation of U.S. patent application Ser. No. 14/972,442, filed Dec. 17, 2015, now U.S. Pat. No. 10,076,452, which is a continuation application of U.S. patent application Ser. No. 12/958,897, filed Dec. 2, 2010, now U.S. Pat. No. 9,259,360, which is a continuation of U.S. application Ser. No. 11/983,264, filed Nov. 8, 2007, now U.S. Pat. No. 7,867,209, which claims the benefit of U.S. Provisional Application No. 60/857,694, filed Nov. 8, 2006, the contents of which are hereby incorporated herein by reference in their entirety.

BACKGROUND OF THE INVENTION

1. Field of the Invention

The present disclosure relates generally to tampon pledgets. More particularly, the present disclosure relates to tampon pledgets that exhibit increased bypass leakage protection.

2. Description of Related Art

Both in-vivo and in-vitro testing has shown that current tampon pledgets do not protect well against bypass leakage. In-vivo testing shows that the typical woman places the tampon pledget too deep into the vaginal canal and is not optimally placed to absorb fluid. In-vitro testing confirms that tampon pledget expansion is not optimal. With both of these insights, it is known that there is a propensity for the tampon pledgets to leak prematurely, i.e., bypass leakage.

There have been many attempts in the prior art to address bypass leakage. Examples include providing a tampon pledget with various pre-expanded, compressed shapes designed to conform to a user's anatomy upon insertion into the vagina. One particular drawback with the tampon pledget having a pre-expanded shape is that it may be difficult to house the pre-shaped pledget in a typical cylindrical applicator barrel due to its shape. Also, once housed in the applicator, the tampon pledget having the pre-expanded shape may exert additional forces on the walls of the applicator barrel due to its shape, which in turn could cause excess friction during expulsion, requiring additional force to expel the tampon pledget from the applicator. The required additional force could make use of the applicator difficult, and in some cases actually cause deformation of the applicator, making its use extremely difficult.

Therefore, there remains a need in the tampon art for a tampon pledget that mitigates or all together prevents bypass leakage, while also avoiding the drawbacks associated with the prior art. The present disclosure meets this need.

SUMMARY OF THE INVENTION

The present disclosure provides a tampon pledget that exhibits increased bypass leakage prevention.

The present disclosure also provides such a tampon pledget that has increased absorption potential at a base of the pledget.

The present disclosure further provides such a tampon pledget that has increased expansion potential at the base of the pledget.

The present disclosure still further provides such a tampon pledget where the desired pledget geometry occurs post-expansion.

The present disclosure yet further provides such a tampon pledget with varying fiber weight distribution across the length and/or width of the pledget.

The present disclosure also provides a method for assembling a tampon pledget that exhibits increased bypass leakage prevention.

These and other advantages and benefits of the present disclosure are provided by a tampon pledget that includes one or more enhanced features that result in the pledget exhibiting increased bypass leakage prevention. These enhanced features may include, but are not limited to, geometry, absorption, or any combinations thereof. The present disclosure also provides one or more methods for constructing a tampon pledget having increased bypass leakage protection.

DETAILED DESCRIPTION OF THE INVENTION

The present disclosure provides a unique tampon pledget designed for various tampon sorts with one or more enhanced features including, but not limited to, increased absorption potential at the base of the pledget, increased expansion potential at the base of the pledget, and any combinations thereof. These enhanced features are achieved by constructing the tampon pledget with certain pad lay-up ratios, fiber weight distribution ratios, and any combinations thereof. As a result of these one or more enhanced features, a tampon pledget having increased bypass leakage protection results. Additionally, the enhanced features do not compromise the desired pledget geometry, or its pre-expansion ability. Therefore, applicator modifications are not required to house the tampon pledget of the present disclosure.

Figure 1:
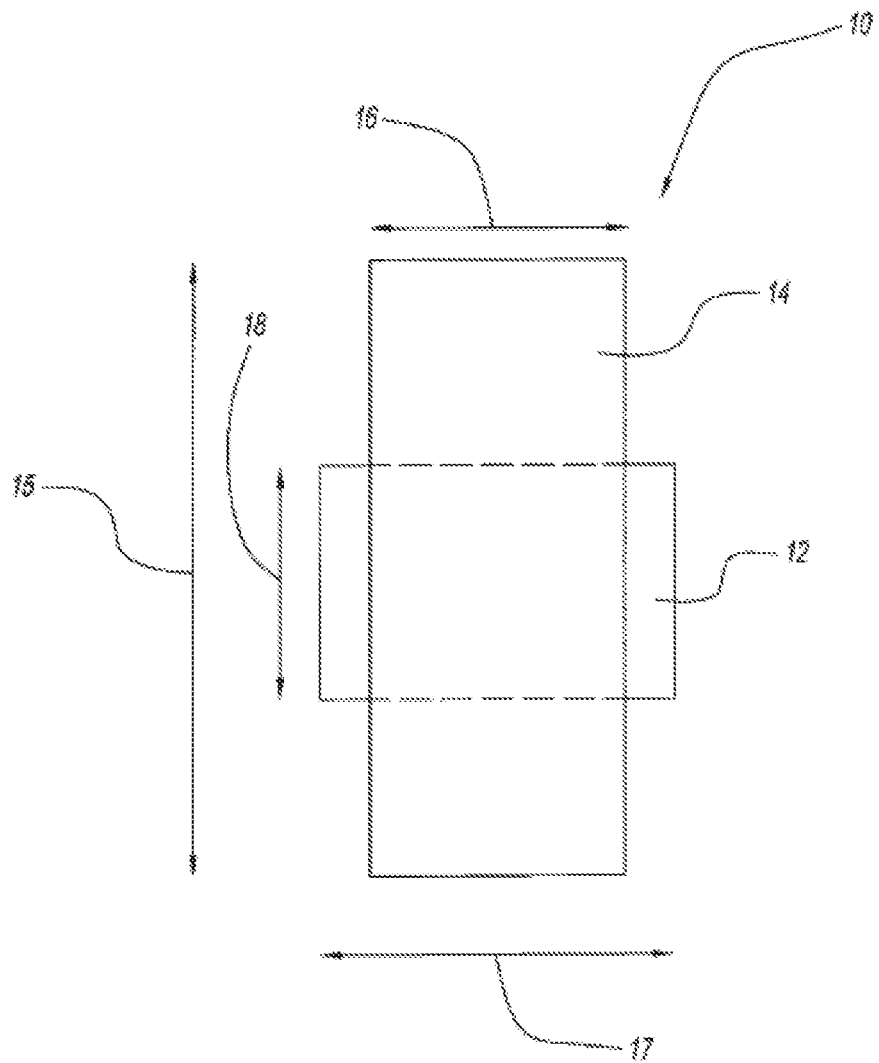
FIG. 1 is top view of pads positioned for a tampon pledget prior to formation of the tampon pledget according to the present disclosure.

Referring to FIG. 1, the present disclosure is exemplified by the pad lay-up represented generally by reference numeral 10. Pad lay-up 10 includes one or more bottom pads 12 and one or more top pads 14. While pad lay-up 10 depicts the one or more bottom pads 12 and one or more top pads 14 in a cross-pad configuration, it should be understood that the pad lay-up can be configured in any suitable shape, including, but not limited to cross, chevron, diamond, circular, oval, square, rectangle, and any combinations thereof.

It has been unexpectedly found that by providing one or more bottom pads 12 with one or more top pads 14 in certain pad lay-up ratios, and based on their respective areas, various desirable tampon pledget configurations can be achieved that provide enhanced bypass leakage protection. Area is defined herein as length times width (without depth as a factor). The pad lay-up ratio is defined as the ratio of the area of one or more bottom pads 12 to the area of one or more top pads 14, with the area of the one or more pads calculated in a single plane. Therefore, while stacking of multiple pads may be done, it does not increase the calculated area of the one or more pads.

Again referring to FIG. 1, the one or more top pads 14 each has a length dimension 15 and a width dimension 16. The one or more bottom pads 12 each have a length dimension 17 and a width dimension 18.

In one embodiment, the one or more top pads 14 each have a length dimension 15 between about 2 inches and about 6 inches. In another embodiment, the one or more top pads 14 each have a length between about 3.5 inches and about 5.0 inches. In yet another embodiment, the one or more top pads 14 each has a length about 4 inches.

In one embodiment, the one or more top pads 14 each have a width dimension 16 between about 1 inches and about 4 inches. In another embodiment, the one or more top pads 14 each have a width between about 1.5 inches and about 3 inches. In yet another embodiment, the one or more top pads 14 each has a width about 2 inches.

In one embodiment, the one or more bottom pads 12 each have a length dimension 17 between about 1 inch and about 4 inches. In another embodiment, the one or more bottom pads 12 each have a length between about 2 inches and about 3 inches. In yet another embodiment, the one or more bottom pads 12 each have a length about 2.5 inches.

In one embodiment, the one or more bottom pads 12 each have a width dimension 18 between about 1 inch and about 4 inches. In another embodiment, the one or more bottom pads 12 each have a width between about 1.5 inches and about 3 inches. In yet another embodiment, the one or more bottom pads 12 each have a width about 2 inches.

In one embodiment of the present disclosure, the pad lay-up ratio is between about 1:1.2 to about 1:2.25. In another embodiment of the present invention, the pad lay-up ratio is about 1:1.6.

Another important aspect of the present disclosure is the fiber weight distribution ratio between the one or more bottom pads 12 and the one or more top pads 14. The fiber weight distribution ratio is defined as the ratio of the fiber weight distribution of the one or more bottom pads 12 to the fiber weight distribution of the one or more top pads 14.

In one embodiment according to the present disclosure, the fiber weight distribution ratio is between about 0.5:1 to about 2:1. In another embodiment according to the present disclosure, the fiber weight distribution ratio is between about 0.75:1 to about 1.5:1. In yet another embodiment according to the present disclosure, the fiber weight distribution ratio is about 1:1.

Suitable materials for use in forming the one or more bottom pads and/or the one or more top pads include, but are not limited to, cellulosic, rayon, cotton, pulp, superabsorbent, absorbent foam, and any combinations thereof.

The tampon pledget may include a liquid permeable coverstock or overwrap material, if desired. Suitable coverstock materials may include, but are not limited to, rayon, cotton, bicomponent fiber, or other suitable natural or synthetic fibers known in the art. Rayon, polyethylene, polypropylene and blends of these are particularly suited for use as a coverstock material.

The following examples demonstrate various embodiments according to the present disclosure. These examples are not intended to limit the scope of the present disclosure.

The pledget shape after exposure to moisture can vary according to the ratios set forth above in accordance with the present disclosure.

Example 1

Figures 2, 3:
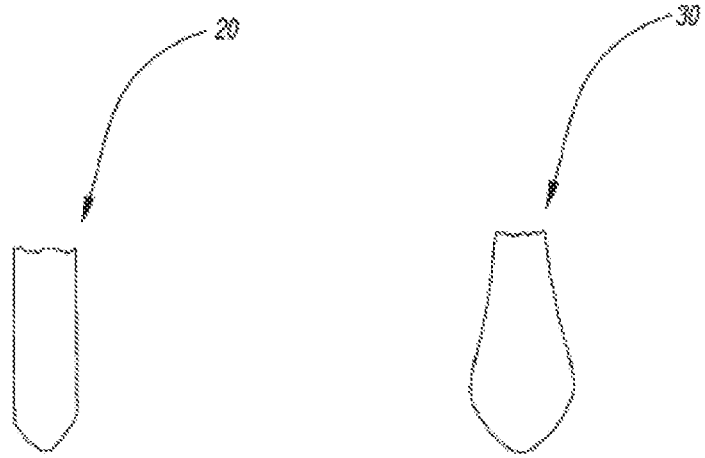
FIG. 2 is a side view of one embodiment of a formed tampon pledget according to the present disclosure.
FIG. 3 is a side view of another embodiment of a formed tampon pledget according to the present disclosure.

A tampon pledget 20 with a pad lay-up ratio of about 1:1.2 and fiber distribution ratio of about 0.75:1 may be constructed. Referring to FIG. 2, tampon pledget 20 with these ratios will have straight wall sides to a slight teardrop or circular shape.

Example 2

A tampon pledget 30 with a pad lay-up ratio of about 1:2.25 and fiber distribution ratio of about 1.5:1 may be constructed. Referring to FIG. 3, tampon pledget 30 with these ratios will have a teardrop shape.

Example 3

Figure 4:
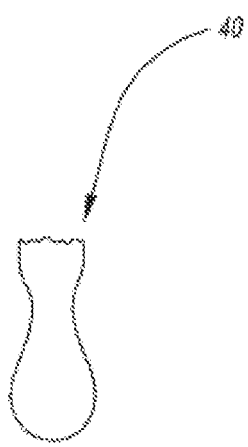
FIG. 4 is a side view of yet another embodiment of a formed tampon pledget according to the present disclosure.

A tampon pledget 40 with a pad lay-up ratio of about 1:1.6 and fiber distribution ratio of about 1:1 may be constructed. Referring to FIG. 4, tampon pledget 40 with these ratios will have a step-down multi-tiered to teardrop shape.

Comparative Examples 4 Through 6

Several commercial tampon pledgets were purchased from retail stores to be used as comparative examples used to compare with tampon pledgets of this present disclosure. Comparative Example 4 tampons or tampon pledgets are Tampax Original (Super) tampons (available from Procter & Gamble); Comparative Example 5 tampons are Tampax Pearl (Super) Unscented tampons (available from Procter & Gamble); and Comparative Example 6 tampons are Kotex Security Super tampons (available from Kimberly Clark).

Example 7

Approximately 60 tampon pledgets were constructed according to the present disclosure invention and tested. These are similar to those described in Example 1. These tampon pledgets were constructed with a pad lay-up ratio of about 1:1.25 and a fiber distribution ratio of about 1:1. Specifically, a bottom pad (2.25"×2.5" from one Galaxy-based web) and a top pad (4"×1.75" of a second Galaxy-based web) were used to construct these tampon pledgets. The top (or inside) pad moisture, as measured by a Halogen Moisture analyzer (Mettler-Toledo) was about 9.78%. The bottom (or outside) pad moisture was 11.55%. Tampon pledget weights were 2.60 g (average)+/−0.03 g (one standard deviation). The tampon pledgets were all constructed as outlined herein, according to the present disclosure.

To form the tampon pledgets of the above Examples, individual pads were arranged in a crosspad configuration according to the present disclosure invention and carefully weighed. Using a Hauni machine, the crosspad tampon pledget was delivered and folded, using an appropriately sized (about 0.25") fluted ram, into a cylindrical shaped transfer tube to form a cylindrical tampon pledget. The pledget was then transferred again using another ram into a warmed oven tube (inside diameter about 0.5", temperature about 220° F.) and then conveyed by a pre-heated IR conveyor oven (Infrared Heating Technologies, LLC). This heated, compressed cylindrical tampon pledget was then transferred into a slightly larger diameter stringer tube. In this tube, a needle was pierced through to permit a Nalan-coated string to be added and tied. Following the addition of string, the tampon pledget was added to a standard Gentle Glide™ plastic applicator. The petals on the applicator were then heated to about 200° F. and shaped, to "close" them. These finished tampon pledgets were stored for at least one day. Then testing, as outlined above, was performed.

Syngyna absorbency was evaluated according to the usual FDA mandated testing procedure, as outlined in the Federal Register, Part 801, 801.430. The Syngyna absorbency, measured for 20 such tampon pledgets, was 10.93+/−0.29 grams, consistent with a super absorbency tampon pledget.

A modified syngyna absorbency test, known as the positive displacement test, was performed. In this modification of the usual FDA procedure, instead of circulating the 27° C. water continuously inside the tube around the condom that encases the tampon pledget, the water was directed to a burette, which was located three inches higher than the top of the syngyna tube. The water level in this burette was adjusted to the zero level at the start of the syngyna experiment. Then, as the tampon pledget expanded to form a shape similar to the teardrop shape of FIG. 3, the water level in the tube increased. This increase was monitored every thirty seconds.

The purpose of this test was to see how rapidly the volume of the tampon pledget expanded during a syngyna absorbency experiment and to compare these results with those for comparable commercial tampon pledgets set forth in Comparative Examples 4 through 6.

Table 1 below provides these results. Twenty tampon pledgets for each of these examples were tested using the procedure outlined above. Since tampon pledget weights vary slightly from manufacturer to manufacturer, Table 1 reports normalized slopes; that is, the rate of volumetric increase vs. time was divided by the average pledget weights, to report the rates of increase in an even-handed manner. As the Table shows, tampon pledgets of the present disclosure exhibit a rate increase that is statistically significantly higher than existing commercial offerings. Notably, the average positive displacement rate is greater than 0.145. Preferably, the average displacement rate is greater than about 0.2.

TABLE I

Positive Displacement Results for Various Super Absorbency Tampons

| Example | Manufacturer | Positive Displacement Rate (ml increase per minute weight of Pledget, (ml/min/gram)) | | |
|---|---|---|---|---|
| | | Average | Standard Deviation | Average % relative to that for Example 7 |
| Comparative 4 | Procter & Gamble | 0.073 | 0.021 | 36.3% |
| Comparative 5 | Procter & Gamble | 0.141 | 0.048 | 69.7% |
| Comparative 6 | Kimberly-Clark | 0.064 | 0.015 | 31.6% |
| Example 7 | Present Invention | 0.202 | 0.034 | 100.0% |

The tampon pledgets according to the present disclosure, as exemplified by Example 7 in Table 1, have the majority of the absorption potential near the bottom of the tampon pledget. As a result of arranging the absorbent material of each tampon pledget in such a manner it promotes an expansion of the pledget that reduces bypass leakage.

The positive displacement in vitro test suggests that tampon pledgets of the present disclosure expand more rapidly than tampon pledgets made by alternative means. Moreover, the observed shapes that these tampon pledgets take during expansion (see Figures), owing to the modified weight and area distributions—together with in vivo results—suggests that tampon pledgets of the present disclosure should be more suitable "plugs" and thus provide more effective bypass leakage prevention.

While the present disclosure has been described with reference to one or more exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the scope thereof.

What is claimed is:

1. A tampon pledget, comprising:
At least one bottom pad having a length that is between about 1 inch and about 4 inches, and a width that is between about 1 inch and about 4 inches;
at least one top pad having a width of about 2 inches and a length of about 4 inches;
a fiber weight distribution ratio of the at least one bottom pad to the at least one top pad being between about 0.75:1 and about 1.5:1; and
wherein prior to folding the at least one bottom pad and the at least one top pad to form a compressed tampon pledget, the at least one top pad and the at least one bottom pad are in a chevron, diamond, circular, oval, square, or rectangle configuration, the chevron, diamond, circular, oval, square, or rectangle configuration having an overlap portion that is formed where the at least one top pad and the at least one bottom pad overlap and a plurality of non-overlap portions that are formed where the at least one top pad and the at least one bottom pad do not overlap
wherein the chevron, diamond, circular, oval, square, or rectangle configuration is folded, compressed, and heated to form a shaped tampon pledget, the tampon pledget having insertion region having an insertion tip end and an insertion rearward end, a main body region having a main forward end and a main rearward end, and a withdrawal region having a withdrawal forward end and withdrawal rearward end, said insertion rearward end is adjacent said main forward end, and said main rearward end is adjacent said withdrawal forward end, the shaped tampon pledget has a maximum diameter of the insertion tip region and the main body region where the insertion rearward end and the main forward end meet, wherein the main body region tapers from the maximum diameter to a minimum diameter and thereafter increases to a middle diameter that is greater than said minimum diameter.

2. The tampon pledget according to claim 1, wherein the dry weight of the tampon pledget is about 2.6 grams.

3. The tampon pledget according to claim 1, wherein the width of the at least one bottom pad is about 2 inches.

4. The tampon pledget according to claim 1, wherein a pad lay-up ratio of an area of the at least one bottom pad to an area of the at least one top pad area is between about 1:1.2 and about 1:2.25.

5. The tampon pledget according to claim 1, wherein the chevron, diamond, circular, oval, square, or rectangle configuration is folded within a fluted ram.

6. The tampon pledget according to claim 1, wherein the heating is to about 220° F.

7. The tampon pledget according to claim 1, wherein at least one of the at least one top pad and the at least one bottom pad comprise cellulose, rayon, cotton, pulp, superabsorbent, absorbent foam, and any combinations thereof.

8. The tampon pledget according to claim 1, wherein the tampon pledget has an average positive displacement rate that is equivalent to a volumetric rate increase of the tampon pledget in a modified syngyna absorbency test divided by a dry weight of the tampon pledget, the average positive displacement rate being greater than about 0.2 ml/min/gram.

9. The tampon pledget according to claim 8, wherein the tampon pledget expands to a slight teardrop shape upon liquid absorption.

10. A tampon pledget, comprising:
a at least one bottom pad having a length and a width;
a at least one top pad having a width and a length;
a fiber weight distribution ratio of the at least one bottom pad to the at least one top pad being between about 0.75:1 and about 1.5:1; and
wherein prior to folding the at least one bottom pad and the at least one top pad to form a compressed tampon pledget, the at least one top pad and the at least one bottom pad are in a chevron, diamond, circular, oval, square, or rectangle configuration, the chevron, diamond, circular, oval, square, or rectangle configuration having an overlap portion that is formed where the at least one top pad and the at least one bottom pad overlap and a plurality of non-overlap portions that are formed where the at least one top pad and the at least one bottom pad do not overlap
wherein the chevron, diamond, circular, oval, square, or rectangle configuration is folded, compressed, and heated to form a shaped tampon pledget, the tampon pledget having insertion tip region having an insertion tip end and an insertion rearward end, a main body region having a main forward end and a main rearward end, and a withdrawal region having a withdrawal forward end and withdrawal rearward end, said insertion rearward end is adjacent said main forward end, and said main rearward end is adjacent said withdrawal forward end, the shaped tampon pledget has a maximum diameter of the insertion tip region and the main body region where the insertion rearward end and the main forward end meet, wherein the main body region tapers from the maximum diameter to a minimum diameter and thereafter increases to a middle diameter that is greater than said minimum diameter.

11. The tampon pledget according to claim 10, wherein the dry weight of the tampon pledget is about 2.6 grams.

12. The tampon pledget according to claim 10, wherein the at least one top pad has a length that is between about 2 inches and about 6 inches.

13. The tampon pledget according to claim 10, wherein the at least one top pad has a width that is between about 1 inch and about 4 inches.

14. The tampon pledget according to claim 10, wherein the at least one bottom pad has a length that is between about 1 inch and about 4 inches, and a width of about 1 inch and a length of about 4 inches.

15. The tampon pledget according to claim 10, wherein a pad lay-up ratio of an area of the at least one bottom pad to an area of the at least one top pad area is between about 1:1.2 and about 1:2.25.

16. The tampon pledget according to claim 10, wherein the chevron, diamond, circular, oval, square, or rectangle configuration is folded within a fluted ram.

17. The tampon pledget according to claim 10, wherein the heating is to about 220° F.

18. The tampon pledget according to claim 10, wherein at least one of the at least one top pad and the at least one bottom pad comprise cellulose, rayon, cotton, pulp, superabsorbent, absorbent foam, and any combinations thereof.

19. The tampon pledget according to claim 10, wherein the tampon pledget has an average positive displacement rate that is equivalent to a volumetric rate increase of the tampon pledget in a modified syngyna absorbency test divided by a dry weight of the tampon pledget, the average positive displacement rate being greater than about 0.2 ml/min/gram.

20. The tampon pledget according to claim 19, wherein the tampon pledget expands to a slight teardrop shape upon liquid absorption.

* * * * *